United States Patent
Cherif-Cheikh

(10) Patent No.: US 6,613,076 B1
(45) Date of Patent: Sep. 2, 2003

(54) IMPLANTABLE INTRALUMINAL DEVICE

(75) Inventor: Roland Cherif-Cheikh, Issy-les-Moulineaux (FR)

(73) Assignee: Societe de Conseils de Recherches et d'Applications Scientifiques SCRAS, Paris (FR)

( * ) Notice: Subject to any disclaimer, the term of this patent is extended or adjusted under 35 U.S.C. 154(b) by 0 days.

(21) Appl. No.: 09/701,617
(22) PCT Filed: Jun. 4, 1999
(86) PCT No.: PCT/FR99/01324
§ 371 (c)(1),
(2), (4) Date: Jan. 29, 2001
(87) PCT Pub. No.: WO99/62426
PCT Pub. Date: Dec. 9, 1999

(30) Foreign Application Priority Data

Jun. 4, 1998 (FR) .............................. 98 07036

(51) Int. Cl.[7] .............................. A61F 2/06; A61B 17/00
(52) U.S. Cl. ...................... 623/1.11; 623/1.36; 606/200
(58) Field of Search ............... 606/200; 623/1.15–1.22, 623/1.36

(56) References Cited

U.S. PATENT DOCUMENTS

| | | | | |
|---|---|---|---|---|
| 3,687,129 A | * | 8/1972 | Nuwayser | ............... 623/1.15 |
| 5,514,176 A | * | 5/1996 | Bosley, Jr. | ............... 623/1.15 |
| 5,695,518 A | * | 12/1997 | Laerum | ............... 606/200 |
| 5,843,164 A | * | 12/1998 | Frantzen et al. | ............... 623/1.36 |
| 5,911,717 A | * | 6/1999 | Jacobsen et al. | ............... 606/1 |
| 6,093,199 A | * | 7/2000 | Brown et al. | ............... 606/200 |
| 6,143,037 A | * | 11/2000 | Goldstein et al. | ............... 623/66 |
| 6,231,581 B1 | * | 5/2001 | Shank et al. | ............... 606/157 |
| 6,231,590 B1 | * | 5/2001 | Slaikeu et al. | ............... 606/200 |
| 6,251,142 B1 | * | 6/2001 | Bernacca et al. | ............... 623/23.57 |
| 6,277,126 B1 | * | 8/2001 | Barry et al. | ............... 606/108 |
| 6,290,719 B1 | * | 9/2001 | Garberoglio | ............... 623/1.15 |

FOREIGN PATENT DOCUMENTS

| | | |
|---|---|---|
| DE | 296 15 067 | 3/1998 |
| WO | WO 90/04982 | 5/1990 |
| WO | WO 91/17744 | 11/1991 |
| WO | WO 98/58599 | 12/1998 |

* cited by examiner

Primary Examiner—David H. Willse
Assistant Examiner—Suzette J. Jackson
(74) Attorney, Agent, or Firm—Young & Thompson

(57) ABSTRACT

A device implantable in the vascular ducts. The device includes an elongated intraluminal element that occupies a section of the vascular lumen so as to increase the speed at the vascular wall at the level of the element without decreasing the blood flow and without exerting any substantial mechanical action on the vascular wall, the element also includes a fixing device in the vascular lumen.

23 Claims, 4 Drawing Sheets

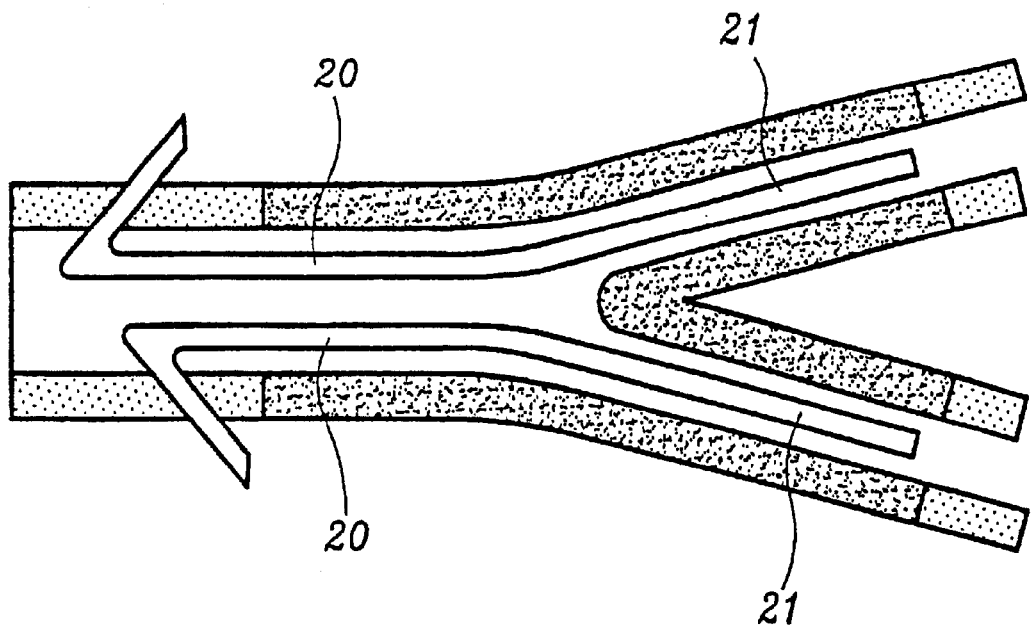
FIG.10
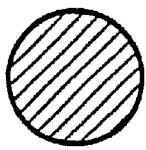  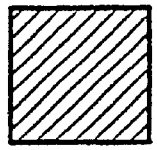  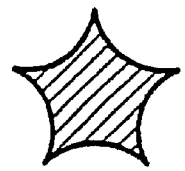
FIG.11A    FIG.11B    FIG.11C

IMPLANTABLE INTRALUMINAL DEVICE

BACKGROUND OF THE INVENTION

Vascular restenosis is the pathological process whereby the vessels become clogged and which corresponds, in particular, to coronary disease. It is associated with the widening or thickening of the internal wall of the arteries which causes a narrowing of the vascular lumen and a reduction in the blood flow or rate. The same process is involved in arterial atheroscleroses, particularly cerebral ones or ones relating to the limbs, particularly the lower limbs.

These diseases can nowadays be treated by interventional cardiology instead of the older method of cardiac surgery. Interventional cardiology consists in introducing an angioplasty catheter into the femoral artery under local anesthetic. Under x-ray control, this catheter can be fitted at the site of the stenosis.

Several types of catheter are used to perform angioplasty, particularly balloon-type or PTCA (Percutaneous Transluminal Coronary Angioplasty) catheters; DCA or RCA (Directional or Rotational Coronary Atherectomy) catheters or LA (Laser Angioplasty) catheters.

These techniques are not very invasive which means that the length of the hospital stay can be reduced.

The major disadvantage is the level of restenosis after three months which is as high as 30 to 50%. In an attempt at avoiding a bypass, which would then often be inevitable, use is nowadays made of spacing implants or stents.

Numerous spacer or stent systems are already in use. These generally consist of a structure (mesh or spring) made of metal and capable of expanding into the shape of a hollow cylinder inside a vessel.

In theory, stents fitted after the angioplasty procedure at the site of the wall that is to be treated are supposed to reduce the level of restenosis after three months. The main reason for this is that the stents very markedly increase the diameter of the vascular lumen. The same degree of restenosis of the vessels will no longer be enough to clog the vessel for the same period after intervention and even beyond, because the initial diameter of the lumen is greater.

Restenosis is the result of various important factors including inflammatory reaction, the elasticity of the vascular walls, mural thrombosis or the proliferation of smooth muscle cells.

Certain recent clinical results obtained with stents have encouraged the belief that the actual level of restenosis has not fallen. Although, for the same period of time after intervention, clogging is avoided, it is possible that the stent is merely delaying the deadline. With the time scales being pushed back in the use of stents, an increasing level of late restenosis requiring reintervention is actually noted.

To face up to this threat the use of an active principle may be associated with the stents, for example by coating the stent with a view to avoiding restenosis through the combined mechanical action of the stent and pharmacological action of the product.

This approach runs into various difficulties including the very small surface area of the stent, which does not allow a great deal of active principle to be associated, or the locating of the product between the stent and the wall of the vessel which either does not correspond to the optimum zone for release or leads to its being taken away rapidly in the blood stream.

Another major difficulty with this solution is that there is no product which has truly been proven to be effective in preventing restenosis, particularly at local intravascular level.

The disappointing results ultimately achieved with stents could be explained by the fact that this mechanical device does not tackle the cause of the restenosis but simply seeks to avoid its consequences.

The various angioplasty techniques, PTCA, DCA, LA or, alternatively, ultrasound, are all traumatic revascularization techniques.

What is in fact involved is spacing the vascular tissues apart, removing plaques of atheroma which will be crushed, destroyed or removed to restore the path for the blood. The zone treated is therefore a zone containing lesions capable of giving rise to post-surgical adhesion phenomena, scarring and tissue formations which could explain the later restenosis.

There is also a risk of thrombosis in this zone after tissue lysis and dilatation.

Implanting a stent directly in contact with this lesion-containing surface could give rise to chronic inflammation phenomena and create aggregation problems. In addition, it is a foreign body placed in direct contact with the tissues on which it exerts permanent mechanical stress. These intravascular tissues are not very tolerant of foreign bodies.

Numerous factors may explain the problems of atherosclerosis after the fitting of a stent.

The risk of causing thrombosis and inflammation is increased by the use of any hollow structure with a non-smooth surface, whether this is in contact with the blood stream in the central flow or at its periphery.

Outside of the treatment of the large coronary blood vessels, there are, with improvements made to stents and vascular access techniques, increasing numbers of radiological applications for perivascular diseases.

All the tissue or cell phenomena are therefore magnified by the reduction in the lumen of the vessel, which increases the risk of restenosis.

Furthermore, it is more difficult to produce and make effective use of a stent in long and/or narrow vasculatures, with greater risks of failure. If the vasculature to be treated is not straight or if there is a branch, fitting a stent is also trickier, if not impossible.

Post-angioplasty restenosis may lead to further clogging which again means that all interventional cardiology treatments are once more to be envisioned. On the other hand, the post-operative reaction of tissue proliferation, if it takes place around a stent, will trap the stent and make it very complicated, if not impossible, depending on the size of the vessel, to resort to any treatment other than bypass surgery.

SUMMARY OF THE INVENTION

The present invention sets out to provide a device which avoids or limits the drawbacks of the prior art and which makes it possible to reduce the risks of stenosis or restenosis, particularly after angioplasty.

Another objective is to provide such a device which is very simple to manufacture and of low cost.

Another objective of the invention is to provide such a device which is easy to fit and fix to the desired site in the vasculature that is to be preserved.

Another objective of the invention is to produce such a device which can be removed far more easily than can a stent.

Another objective of the invention is to provide such a device which can deliver a significant amount of an active principle which is effective against stenosis or restenosis.

Yet another objective is to provide a device which is resolvable and can disappear by itself, after a certain length of time.

Yet another objective of the invention is to provide such a device which limits or eliminates mechanical action on the wall of the vessel.

Another objective of the invention is to provide such a device which can easily be manufactured in different sizes and, advantageously, allows one and the same device of a given size to be used for a relatively broad range of lumen diameters.

The subject of the present invention is a device that can be implanted in the vasculature, characterized in that it comprises an elongate intraluminal element capable, in a portion of the vascular lumen, of occupying a volume of this lumen without reducing the blood flow and without exerting appreciable mechanical action, and preferably without exerting any mechanical action, on the vascular wall, said element being associated with a means of fixing into the vascular lumen.

This device is preferably in the form of a rod, preferably solid and smooth or uniform in its longitudinal surface, of preferably constant diameter and cross section, one of the ends of which is free; the other end being either held by contact with the wall of the vessel or implanted in this wall by said fixing means; this being directly or via an associated anchoring zone.

The objective of this device is to modify the influence of the vascular circulation exerted locally on the treated wall without reducing the blood flow and without direct mechanical action on this wall of the vessel. This device more particularly makes it possible to increase the speed at which the blood flows at the vascular wall. This modification without reducing the flow rate is made possible by the elasticity of the vessel in which the endothelium and the intima participate.

Although there is not currently any definite explanation for the effectiveness of the device according to the invention, it is believed that the reaction that follows the fitting of a spacer device such as a stent will lead to late restenosis because of the increase in the thickness of the intima of the vessel.

This hyperplasic intima (HI) is controlled by the endothelium. It would seem that this proliferation decreases if the blood flow is high and increases if this flow is low. When a stent is used, the distension of the tissue that it causes could inhibit this mediation of proliferation. This is because the vascular tissues at the local site are then subjected to mechanical stretching which, in spite of the increase in flow obtained by the stent, does not reflect the normal blood pressure at this site on the vascular wall.

Any device which presses against the vessel over a large area such as a stent on the atherosclerosis zone, thus constitutes an area of mechanical distension which could therefore ultimately prevent regulation of the proliferation of the intima and present a risk of restenosis.

Post-angioplasty restenosis is therefore a remodelling or hyperplasia of the intima. To avoid it, this proliferation and migration of smooth muscle cells needs therefore to be inhibited.

This vasculo-proliferative disorder is a relatively slow process which will take at least three months to clog a vessel (and far longer if there is a stent).

There is therefore, in all events, a period of time during which, following the angioplasty, the blood flow is restored.

The device according to the invention will, during this essential period and possibly beyond it, make it possible to alter the blood circulation in the zone which has undergone the interventional revascularization procedure without spacing apart or direct contact with the lesion-containing wall. Thus, the increase in the blood flow will be able to fully play out its role of slowing the proliferation of the intima and avoiding restenosis. A stimulus to biological regulation is thus proposed while avoiding the mechanical contact device which could perturb this regulation.

The means proposed by the device of the invention is the installing in this part of the bloodstream of a device which will occupy a volume and therefore force the newly restored flow to exert action on the wall of the vessel which will allow the biological mechanism to regulate cell proliferation to avoid restenosis.

One of the important features of the device is therefore that it is a "non-stent" device, that is to say that it avoids any appreciable mechanical action on the wall of the affected portion of the vessel likely to inhibit the regulating effectiveness of the blood pressure and, preferably, avoids any permanent contact.

Thus, even more advantageously, the device can be held on the surface or anchored into the wall of the vessel upstream of the zone that is to be treated, so that only the element or rod in the blood stream is in the traumatic zone without any appreciable contact or even without any contact with the wall.

As the device may consist of a solid rod, it is very easy to establish and control the volume occupied with respect to the diameter of the vessels and thus to regulate the blood circulation parameters.

For a vessel of given lumen diameter, the larger the diameter of the device, the more the speed of the blood will be increased in a given proportion associated with the elasticity and reactiveness of the cell layers that make up the vessel. Beyond that, the device could actually reduce the blood flow.

To reduce this risk, this solid rod will preferably be made with a smooth surface in the longitudinal direction, which will encourage the blood to flow. By comparison with the mesh or hollow devices, this solid and smooth device also makes it possible to reduce the risks of thrombosis or clotting.

This solid and smooth shape therefore makes it possible to envisage a volume higher than a hollow shape or a shape with an irregular surface, without risking reducing the flow.

The device will preferably occupy a volume such that its cross-sectional area may be between 5 and 50% of the area of the lumen of the vessel. This percentage may be adapted according to the magnitude of the stenosis, its treatment and its length. This percentage may vary according to the use (coronary or peripheral vessel).

As a preference, the cross section of the device is between 10 and 20% of the cross section of the vessel in which it is implanted. This cross section may be cylindrical, oval, square or have any other shape, for example a star-shape with the ends angular and inside corners rounded so as to reduce the possible area for contact with the vascular wall while at the same time encouraging the blood to flow round the periphery.

As a preference, the device according to the invention has a diameter of between 0.5 and 2 mm.

Its length is preferably between 0.5 and 15 cm in length.

The elongate structure of the device may be rigid, semi-rigid or supple, particularly when it is very long.

The system for anchoring into the wall of the vessel, by contact or by being implanted, makes it possible to avoid resting or support on the vessel in the zone that is to be treated. This may be multi-point or circular anchorage but preferably two anchoring points for anchorage by contact, or just one anchoring point for implantation, will be used so as to disrupt the blood flow and the reactions of the vascular wall as little as possible. In any case, even in the event of contact retention, the resting will be light rather than causing mechanical stretching as is the case with stents.

This anchorage may be achieved by extending, in the lumen of the vessel, an anchoring zone upstream of the element or rod of the device which will move away to touch the wall of the vessel at least at two points when released from an administration system such as a hollow needle or a catheter for example, the device being forced to keep a straight shape in its anchoring zone until it has been released.

This spacing will differ according to the diameter of the lumen, which will make the device useable regardless of the diameter of the vessel.

In addition, rather than the extension it is generally the jamming, across the flow, of the anchoring zone, controlled by the free end of the rod, which provides positioning.

The device can be fitted and released in its insertion zone by systems equivalent to those used for positioning stents, that is to say fitting systems with interventional catheters and/or active guide wires.

The transitional movement of the one of these elements with respect to the other will release the device. As the device may be wire-like, the total diameter of the catheter may therefore by even smaller than that of the catheters used for stents.

Such a mechanism for releasing the anchorage may also be used to allow the anchoring means to be implanted in the wall of the vessel.

This type of anchorage can also be obtained by injecting a needle containing the device, possibly with an anchorage zone, through the lumen. This insertion system is likenable to the one described in applications FR 96/14755 and PCT FR 97/02182. The needle, the device and the activation guide rod will be installed in an interventional catheter equivalent to those used for fitting stents. The device may also be part of the guide which will remain in position.

The needle can be pushed through the wall of the vessel, the guide or wire allowing the device or its anchoring means to be released in the peripheral zone of the vessel. The needle is then withdrawn from the wall then the interventional catheter will thus release the fixed device into the blood flow.

Said device will then preferably be supple or flexible enough to be positioned by the blood flow.

The mechanism for releasing the device or its anchorage may be controlled from the outside by the same transmission systems as release a stent at the end of the catheter, that is to say withdrawing the catheter or moving the guide or wire forward.

According to another insertion mechanism, the device is itself produced in the form of a needle which is solid at one of its ends corresponding to the anchoring zone and which can be injected into the wall by withdrawing a guide catheter. If the device is supple or flexible, this withdrawal then causes the release of the elongate element of the device as far as the other end. If the device is more rigid, it can be released by the catheter guide before the anchoring zone is implanted.

The pointed needle-shaped end which constitutes the anchoring means may be non-rectilinear with respect to the rod in the blood flow so as to encourage its implantation and the positioning of the free rod downstream in the vessel. An arrowhead or barbed-hook shape may hold the anchoring zone in the vascular wall.

The device may also simply be rectilinear and planted in the wall of the vessel where it will be held simply by the pressure of the tissue and by scaring. It is possible to envision for the anchoring part not to be smooth but to have roughnesses encouraging it to be held in the tissue. Alignment of the supple element in the flow will give rise to an acute angle with respect to its insertion, which will encourage it to be held more firmly.

The anchoring means can expand so that it is implanted in the wall from the time that the catheter guide is withdrawn.

As this is a non-hollow device, the insert or guide wire is no longer necessary, and the entire implantation system device can therefore be more slender than the stent and implantation system assembly. The intervention catheter will therefore be of smaller diameter, which will allow easier intervention and access to narrower sites than was the case with devices of the stent type.

To treat a branched zone, with two or more passages, and regardless of its shape, recourse may be had to the implanting of several, preferably supple or flexible, devices in the common trunk, each of which will have its end placed inside one of the passages that is to be treated. The device will therefore adapt itself to all vascular arrangements far more readily than do stents, without entailing special shapes.

As the device can be installed just after the angioplasty, its favorable action on the pressure can take effect right from the start of and throughout the period at risk from restenosis.

It is possible to envision various shapes of device which may or may not be intended to be withdrawn or eliminated once they have exerted their action.

In certain instances, it may be desirable to have the device disappear after a period of 3 to 6 months.

The consequence of this withdrawal or this elimination could be a variation in local pressure but this would have no effect on a stabilized zone and in addition will be compensated for or reduced by the elasticity of the vessel.

In the case of withdrawal, given the preferably smooth and solid shape of the device and its position without wall separation, all the problems associated with restenosis around a stent are avoided and, even in the event of restenosis, withdrawal remains simple and instantly leads to recanalization which once again allows all the angioplasty treatments.

This withdrawal can be performed by an endovascular route by grasping or fixing the anchoring zone (contact or insertion, for example, using grippers or a hook) followed by extraction, or alternatively by a perivascular route also by pulling on the anchoring zone.

The angle at which the anchoring means is positioned, by contact or insertion, can allow easy withdrawal simply by pulling on the anchoring zone. It is possible to provide a fixing zone upstream of the anchoring zone for subsequent withdrawal.

The device may, for example, consist of a stainless steel wire of constant diameter. It can be made of the materials conventionally used in stents, particularly metals and their alloys.

The device can therefore act over a longer length than can stents and can be positioned in the vessel regardless of their diameter and their shape. Depending on the materials used, on its diameter and on its suppleness, it will actually adapt itself to suit the vasculature.

Given the very small diameter and size of the device, it is possible, where the vasculature branches, to implant a number of devices using one or two interventional catheters. The single catheter could, for example, release two guide tubes which will separate into each of the vascular passages allowing the free rod of the devices to be released, followed by the release of the two means of anchoring into the common trunk.

The device can be made of plastic because no mechanical stress is exerted on this device. It may, for example, be made with the materials used for non-biodegradable sutures, nylon or polysulfone.

The device may be made with all biomaterials likely to improve its local tolerance, for example Teflon (PTFE), silicone, etc.

It may just as easily be made with biodegradable suture materials, that is to say, for example, PLGA (polylactide co-glycolide).

The advantage of using PLGA is that a device is obtained whose life in the blood flow is known (for example 3 months) and which will be naturally eliminated thereafter without any withdrawal intervention.

Another possible advantage of using PLGA or some other biodegradable material is the possibility of associating with the device an active principle (AP) capable of avoiding or reducing the risks of restenosis.

The entire volume of the device (including any anchoring system) can be used as a reservoir for PLGA formulation so as to have both endovascular and perivascular diffusion of the AP.

Aside from biomaterials, biodegradable or otherwise, plastics or metals that can be used for the device, it is possible to resort to a hydrophilic or some other coating system to improve the biocompatability or make the surface of the elongate element non-stick. For example, the device may be covered with hyaluronic acid, collagen, PEG (polyethylene glycol), glycerol, hydrogel, etc. The metal surface may equally be silicone coated or undergo a surfacing operation.

Use may also be made of all the surface modification processes envisioned for stents.

It is also possible to coat a metal or plastic device with a PLGA which may contain an AP; for example Lanreotide, hydrocortisone, a glucocorticoid, a cystostatic (anticancer) product or any AP envisioned for use with stents.

Thus, the local and systemic effect of the product will be obtained and the diameter of the device and therefore its effect on the local circulation will be reduced once the PLGA or any other delaying excipients in the coating have been eliminated.

Given the shape of the devices, they may advantageously be manufactured by extrusion or die-forming, using exactly the same techniques as those used to produce catheters, tubes, wires, sutures, etc. The shape of the die used and the drawing operation will determine the constant cross section and shape of the device (round, square or star-shaped).

The cost of manufacturing this device will therefore be extremely low; this will allow more wide-scale use and the production of models specific to each case.

Another subject of the invention is a method for implanting the device which employs an interventional catheter of the same type as those used for fitting stents, as described hereinabove. This catheter may, as necessary, be withdrawn by external means releasing the anchoring zone, then the entire device up to the anchoring zone.

The anchoring zone may, for fitting, be implanted using a needle placed inside the catheter.

Another object of the invention is the therapeutic process consisting, following an angioplasty, in installing in the flow through the vascular lumen a device as described hereinabove, the volume of which will lead to a variation in the local circulation of liquid without this device interfering, through contact, with the vascular walls.

This process therefore makes it possible to create a stimulus for regulation of vascular proliferation in sections of vessels which have been subjected to angioplasty, which will make it possible to avoid vascular restenosis.

Implantation may be done in such a way that the anchoring means are located upstream of the elongate element of the device in the direction of the flow or, on the other hand, downstream, with the free end of the elongate element then arranged upstream.

As a preference, the fixing, using an anchoring zone, will be outside of the actual section which has undergone the angioplasty. However, because the fixing means exert no appreciable mechanical action on the vascular wall, as compared with the effect of a stent or similar device, the device could just as easily be fixed in the region of a portion which has undergone angioplasty.

In an improved form of the process according to the invention, this device can be withdrawn after use by releasing the fixing means, for example using a withdrawal device in a catheter.

However, in another implementation of the process according to the invention, the device can be left to be resorbed when it is made of an appropriate material, until it ends up disappearing.

The process according to the invention may, at the same time, comprise delivery of an active principle likely to oppose restenosis and, advantageously, this active principle can be carried and released by the device itself.

BRIEF DESCRIPTION OF THE DRAWINGS

Other advantages and features of the invention will become apparent from the reading of the following description which is given by way of nonlimiting example and with reference to the appended drawings, in which:

FIG. 10 depicts a view of two devices implanted in branched vasculature; and

FIGS. 11a, 11b and 11c depict a diagrammatic view in cross section of various possible shapes of the cross section of the elongate rod of the device.

DETAILED DESCRIPTION OF THE PREFERRED EMBODIMENT

Figure 1:
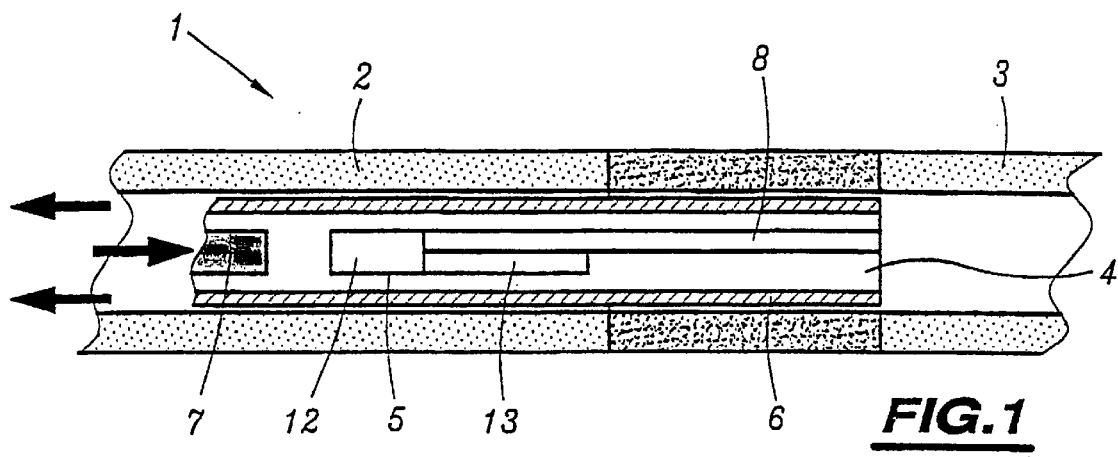
FIG. 1 depicts a diagrammatic view in longitudinal section of a device in the process of being implanted using a catheter.

As depicted diagrammatically in the drawing, a vessel (1) has a first zone (2) in which the vascular wall is normal given the condition and age of the patient, followed by a portion (3) in which the wall has undergone angioplasty restoring the lumen (4) of this vessel to a sufficient diameter.

The device (5) according to the invention is contained at the end of an intravascular catheter (6) inside which a conventional intervention and guide rod or wire (7) placed in alignment with the device (5) can slide. The other end, not depicted, of the catheter and of the wire (7) is located outside the body of the patient and is equipped with the customary maneuvering means as described, for example, in the aforementioned patent applications. It will therefore be understood that if the guide (7) is left in position and the catheter (6) is withdrawn to the left, the catheter will gradually release the device (5).

The device (5) is made, for example, of metal and has an elongate element (8) one end of which is free and, connected to the elongate element (8), means (9) comprising a first straight part (10) extending the element (8) and ending, after an elbow (11), at a free anterior arm (12). Extending at the elbow is another part (13) in the form of a branch, ending with a free arm (14) following an elbow (15).

Figure 2:
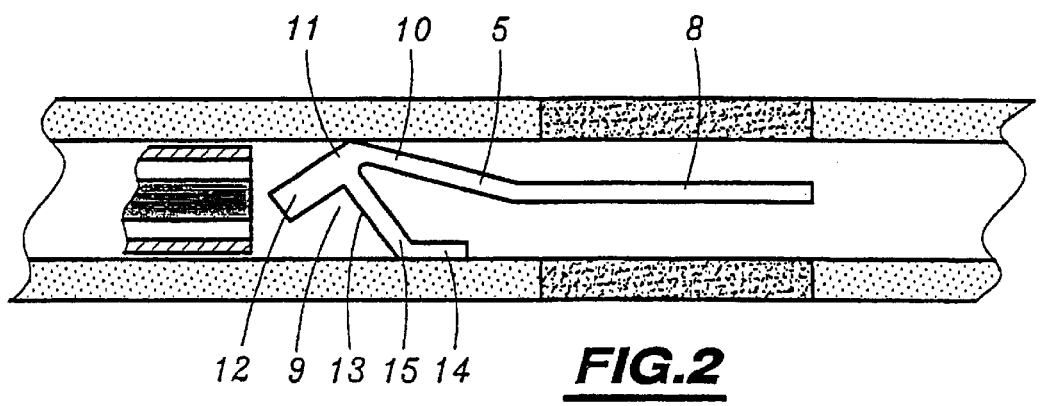
FIG. 2 depicts a view of this device, released.

This device is semirigid and, when trapped inside the catheter (6), occupies an essentially rectilinear shape in which the extensions (10, 13) and the tabs (12, 14) are not very, if at all, inclined with respect to the cylindrical elongate element (8). When the device is released, it spontaneously adopts the shape depicted in FIG. 2 in which the part (5) is oblique with respect to the extension (8) as far as the elbow (11), while the branch (13) separates away from the elbow (11) to come into contact with the vascular wall via the elbow (15) and the tab (14) which extends it. The anterior tab (12) inclines itself forward again and toward the center of the vascular lumen and thus forms an element which can be grasped by an appropriate extraction device.

It will be understood that in this embodiment, when the device is released the elbows (11) and (15) will come into contact, at points located in a diametrically opposed plane, with the vascular wall and, by virtue of their residual elasticity, will hold the device in its position in which the elongate element (8) is sequent in the lumen at the site of the portion (3).

Through a choice of the volume occupied by the extension (8) which choice is appropriate and in accordance with the invention, a variation in the speed of the liquid flowing through the vascular lumen in the zone surrounding it and, thus, the desired therapeutic effect, are achieved.

Figure 3:
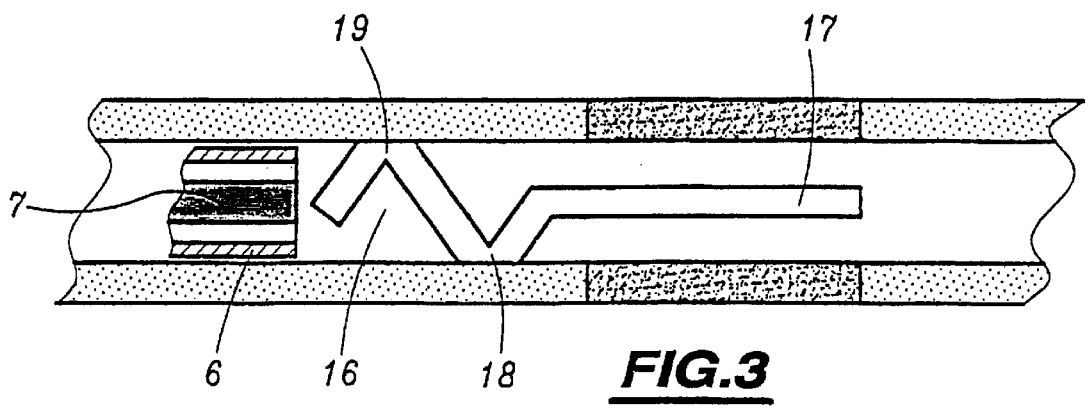
FIG. 3 depicts a view of a device according to an alternative form of FIG. 2.

Reference is made to FIG. 3 which depicts a simpler variant of the device according to the invention, in which the device (16) has the elongate element in the form of a free rod (17) followed by an anchoring means in the shape of an S determining two elbows (18, 19) via which the device rests and is held against the vascular wall. This device has a practically straight shape when it is against the inside of the catheter and deploys to adopt the shape depicted in the drawing when it has been released through the same process as the one described for FIGS. 1 and 2.

Figure 4:
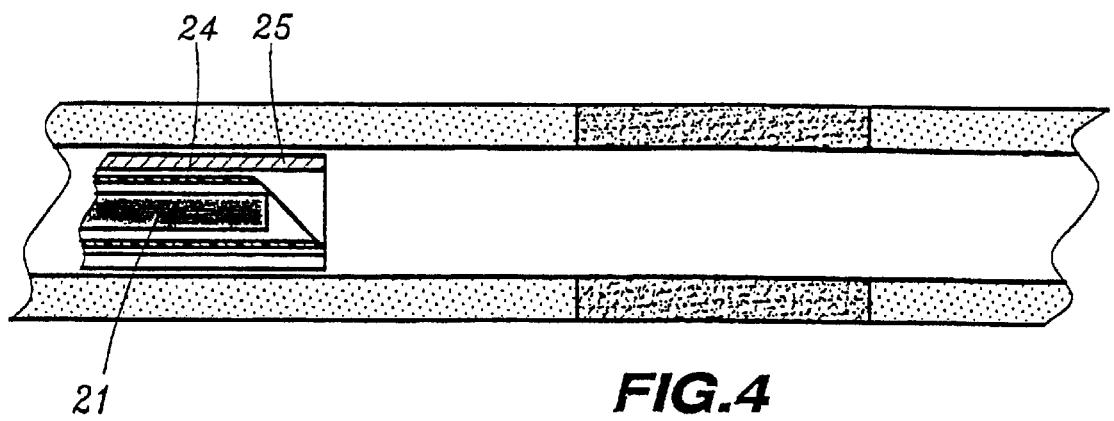
FIG. 4 depicts a cross-sectional view of another device according to the invention, in the process of being located.
Figure 5:
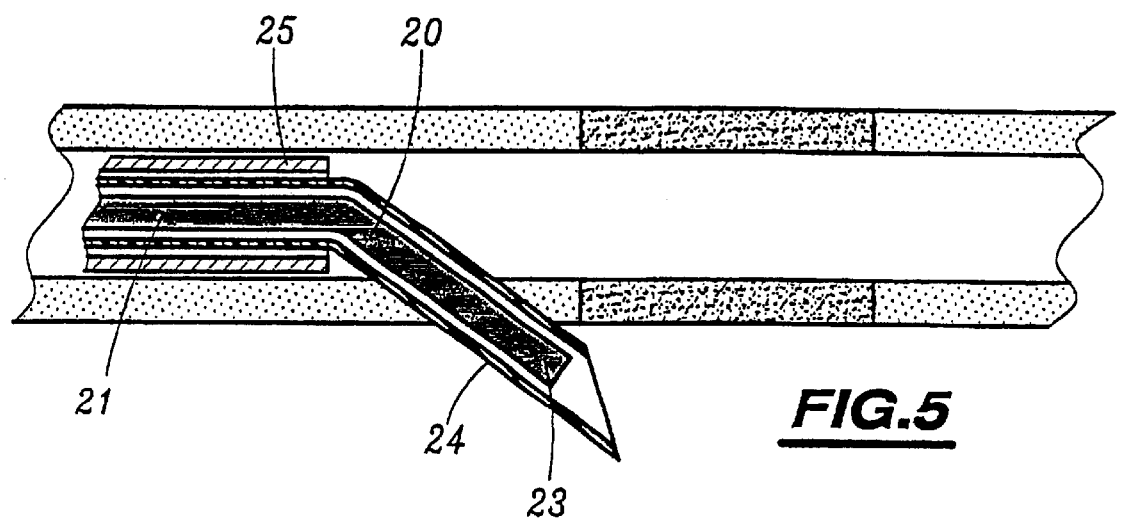
FIG. 5 depicts a cross-sectional view of an intermediate stage of implantation.
Figure 6:
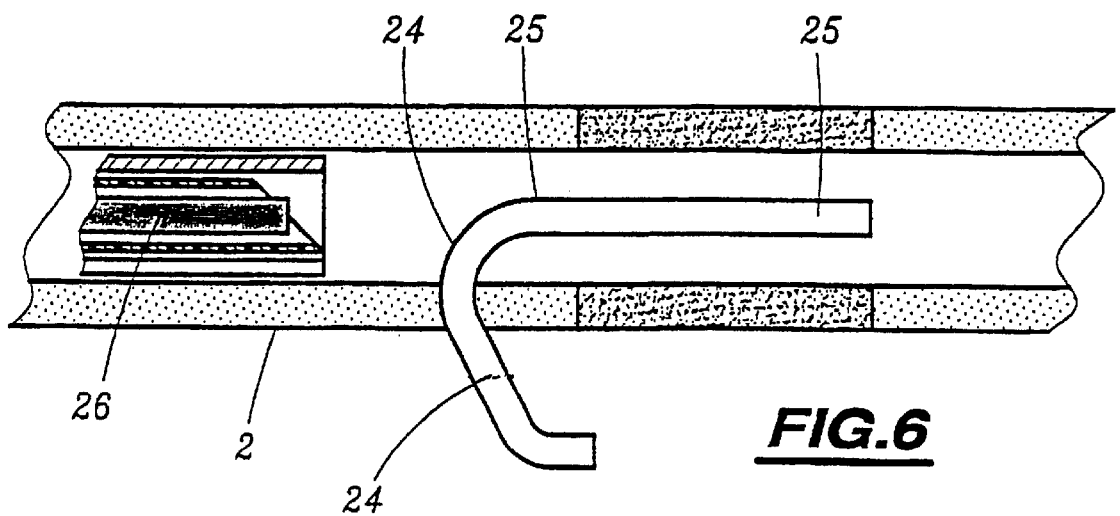
FIG. 6 depicts a cross-sectional view of this device in the implanted state.

Reference is now made to FIGS. 4 to 6 which depict a device according to another form of embodiment. This device (20) has an elongate rod (21) continued by an anchoring means (22) obtained by an elbow-shaped deformation of which a part (23) passes through the vascular wall (2).

To fit such a device, the semirigid device is inserted into an implantation needle (24) contained in a catheter (25). This needle is of a known type which, when protruding sufficiently from the catheter (24), pushed back by the operating means located outside the body, forms an elbow which directs it obliquely with respect to the vascular lumen until it has passed through the vascular wall as can be seen in FIG. 5. Once the needle is in this position, a guide wire, not depicted, is used to hold the device (20) in this position then the needle (24) is retracted back into the catheter (25) so that the device remains in place, anchored into the vascular wall by passing through the wall as depicted in FIG. 6, the inherent elasticity of the device allowing it to adopt the shape depicted in FIG. 6.

Figure 7:
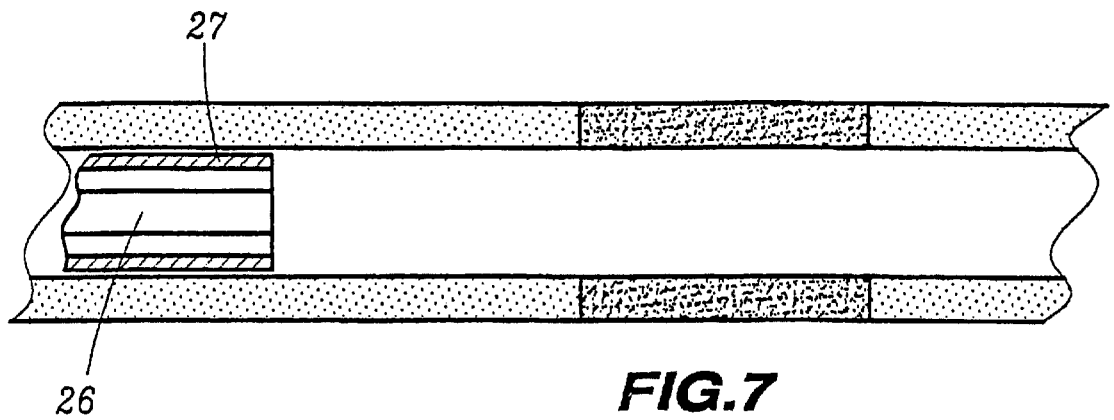
FIG. 7 depicts a cross-sectional view of the end of another device according to the invention in the process of being located.
Figure 8:
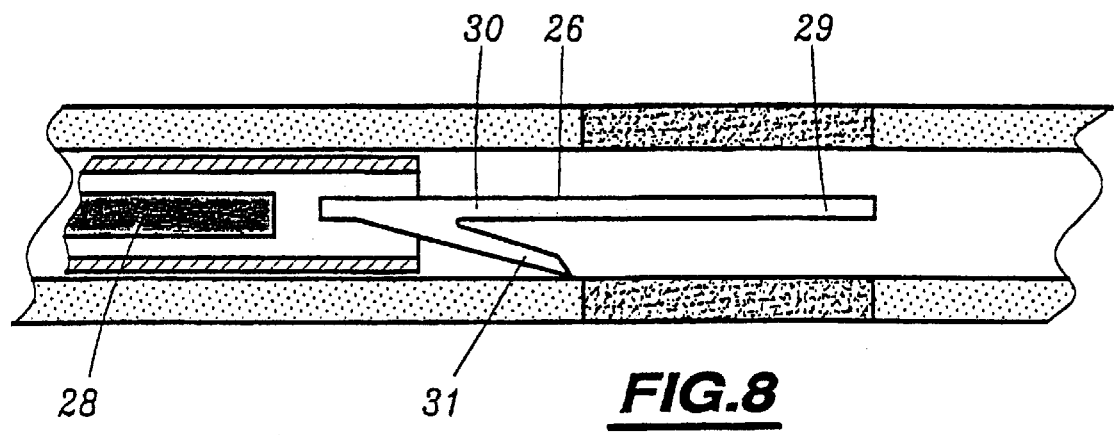
FIG. 8 depicts a view of this device at the time of implanting.
Figure 9:
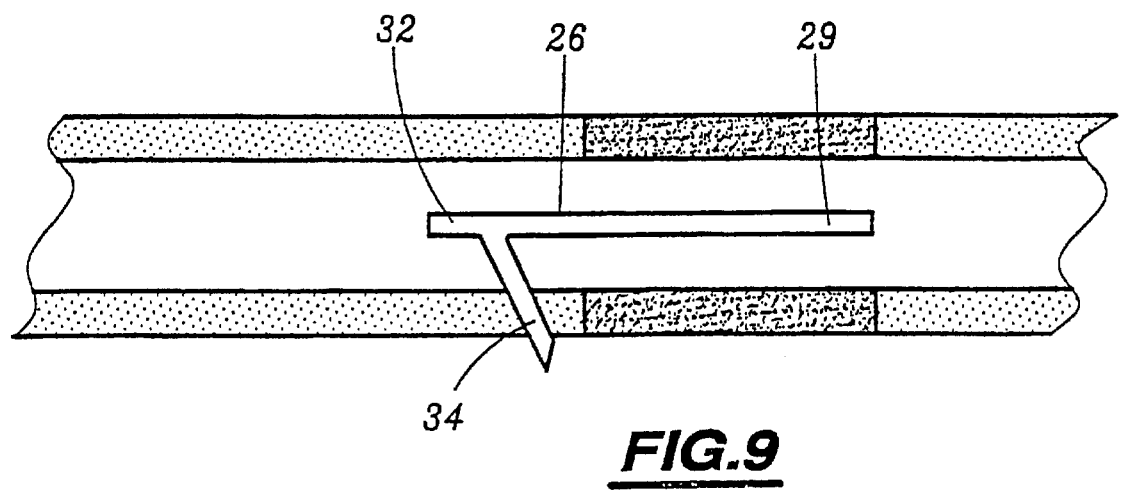
FIG. 9 depicts a view of the device once it has been implanted.

Reference is now made to FIGS. 7 to 9 which depict a device according to another form of embodiment of the invention. The device (26) is initially contained and constrained in a catheter (27) from which it can be extracted, with the catheter remaining fixed, by a guide (28) sliding in the catheter. The device also comprises an elongate rod (29) and anchoring means (30) comprising an arm (31) ending in a point like a barb. When the device is released, this arm separates obliquely from the remaining straight part of the device and, under the thrust of the guide wire (28), its pointed end (34) penetrates the vascular wall and attaches therein. The anterior end (32) of the device is also straight and extends the rod (29) to form a connecting zone allowing it to be grasped by a gripping means, such as a gripper for example, led in by a catheter when there is a desire to extract the device.

Reference is made to FIG. 10 which shows two devices (20) according to the form of embodiment sketched diagrammatically in FIG. 6 and installed in such a way that each of the two elongate rods (21) is in one of the vasculatures that is to be treated.

Reference is now made to FIG. 11 which shows three possible shapes of the device corresponding to the cross section of said device, for example in the elongate rod part.

The invention is not restricted to this implantation process but should be understood as covering all devices of elongate solid shape, with smooth surface and constant or non-constant cross section and diameter, held directly or attached into the wall of the vessel outside the stenosis zone or via an anchorage zone that works by contact or insertion. The anchorage zone that works by contact will be supported by the walls of the vessel at least at two bearing points. The anchorage zone that works by insertion will have just one point of contact. In both instances, no stent effect of separating the vascular walls is sought.

The device will be usable in blood vessels and in all ducts containing a biological fluid where stents can be used and where there is an endothelium likely to react to the local circulation.

What is claimed is:

1. A device for implantation in the vasculature, comprising:
    an elongate intraluminal element implantable in a portion of a vascular lumen, said elongate intraluminal element occupying a volume of said vascular lumen without reducing the blood flow through said vascular lumen and without exerting appreciable mechanical action on a vascular wall, said element being associated with a means of fixing into the vascular lumen, said element being solid with a smooth surface and with a constant diameter and cross section, with a cylindrical, oval, square, star-shaped or flower-shaped cross section.

2. The device as claimed in claim 1 having a proximal end or anchoring zone that can be fixed to or through the wall of the vessel, followed by a rod and by a distal end which is free in the blood stream so that only the anchoring zone is in permanent contact with the tissues of the vessel.

3. The device as claimed in claim 1, with a diameter of 0.5 to 2 mm and a length of 0.5 to 15 cm.

4. The device as claimed in claim 1, with a cross section of between 5 and 50% of the cross section of the vessel in which it is implanted.

5. The device as claimed in claim 1, with a cross section of between 10 and 20% of the cross section of the vessel in which it is implanted.

6. The device as claimed in claim 1, in which said fixing means comprises an anchoring zone made of a material which, when the device is placed in the vascular lumen, allows a change in shape leading to at least two points of contact with the vascular wall.

7. The device as claimed in claim 6, characterized in that it is deformable into a roughly straight position so that it can be fitted using a needle or a catheter.

8. The device as claimed in claim 1, in which said fixing means (23, 31) comprises an anchoring zone allowing direct implantation in the wall of the vessel.

9. The device as claimed in claim 8, characterized in that said anchoring zone is made of a material allowing it to deform when the device is placed in the vascular lumen.

10. The device as claimed in claim 1, in which said fixing means are arranged to allow said device to be withdrawn.

11. The device as claimed in claim 1, made of stainless steel, alloy or plastic.

12. The device as claimed in claim 11, the surface of which is hydrophilic, silicone coated or surfaced.

13. The device as claimed in claim 1, made of nylon, polysulfone, of Teflon or of silicone.

14. The device as claimed in claim 1, made of PLGA.

15. The device as claimed in claim 1, the surface of which is covered with a coating.

16. The device as claimed in claim 15, in which said coating is made of hyaluronic acid, collagen, PEG, glycol, hydrogel or PLGA.

17. The device as claimed in claim 1, containing a releasable active principle.

18. The device as claimed in claim 17 in which the active principle is Lanreotide, hydrocortisone, a glucocorticoid or a cytostatic.

19. The device as claimed in claim 1 produced by melt extrusion or co-extrusion or by die-forming and drawing.

20. A device for implantation in a vasculature, comprising:

a solid elongated member having first and second ends; and an anchoring device connected to the second end of the elongate member, the anchoring device comprising first and second arms elastically connected to one another at a first elbow, an end of the first arm opposite the elbow being elastically connected to the second end of the elongate member so that while in a relaxed position a smallest included angle between the first arm and the elongate member is obtuse.

21. The device according to claim 20, further comprising a third arm extending from said first elbow.

22. The device according to claim 20, wherein the second arm comprises first and second sections elastically connected to one another at a second elbow.

23. The device according to claim 20, wherein the elongate member and the first and second arms have a same cross-section.

* * * * *